United States Patent [19]

Body et al.

[11] 4,190,332
[45] Feb. 26, 1980

[54] METHOD AND APPARATUS FOR CONTROLLING VISUAL REFRACTIVE STATE OF THE EYE

[75] Inventors: Richard H. Body, Centreville; Edwin W. Evers, Reston, both of Va.

[73] Assignee: Acuity Systems, Incorporated, Reston, Va.

[21] Appl. No.: 842,173

[22] Filed: Oct. 14, 1977

[51] Int. Cl.² ............................................. A61B 3/10
[52] U.S. Cl. ........................................ 351/13; 351/39
[58] Field of Search ................................ 351/13, 39

[56] References Cited

U.S. PATENT DOCUMENTS

| 3,836,238 | 9/1974 | Munnerlyn et al. | 351/39 X |
| 3,843,240 | 10/1974 | Cornsweet | 351/13 X |
| 3,883,233 | 5/1975 | Guilino | 351/13 X |

OTHER PUBLICATIONS

Knoll et al., "The Ophthalmetron . . .," *Amer. J. Optom & Arch of Amer. Acad. of Optom*, Feb. 1972, pp. 122–128.
Leibowitz et al., "Anamalous . . . Accommodation," *Science*, vol. 189, Aug. 1975, pp. 646–648.
Leibowitz et al., "Night . . . Accommodation," *JOSA*, vol. 65, No. 10, Oct. 1975, pp. 1121–1128.
Hennessy, "Instrument Myopia," *JOSA*, vol. 65, No. 10, Oct. 1977, pp. 1114–1120.
Mathew Aplern, "The Stimulus," pp. 246–247.

*Primary Examiner*—Paul A. Sacher
*Attorney, Agent, or Firm*—Cushman, Darby & Cushman

[57] ABSTRACT

A method and apparatus are disclosed for controlling the refractive state of the eye. The image of a visual target is continuously positioned close to, but offset from, the retinal plane of the eye to be controlled. The offset is in such a direction from the retina that as the eye attempts to focus on the image, the refractive state of the eye will change toward the desired goal. To increase the effectiveness of the method and apparatus, the position of the image is continually varied along the optical axis.

26 Claims, 2 Drawing Figures

METHOD AND APPARATUS FOR CONTROLLING VISUAL REFRACTIVE STATE OF THE EYE

This application relates generally to a method and apparatus for controlling the focus of the eye. The degree of such focus is commonly called the state of eye "accommodation" and is, at least in part, a measure of the effort being exerted by eye muscles in their attempt to focus a sharp image on the eye's retina.

For both medical and research purposes, it is often necessary to control the accommodation of a patient's eye. One such situation where control is necessary is when an ophthalmologist or optometrist examines a patient to determine whether or not glasses are needed. For distance vision, it is necessary for the patient to focus the eye on a plane as far distant as possible—theoretically at infinity for a perfectly normal eye. In the art, this is called the far point (the most distant point that a person can see clearly). The lens power that the practitioner prescribes should be such that the patient's far point with correction is at infinity; therefore, distant objects should be sharply focused on the eye's retina.

Since certain terms will be frequently referred to in this patent, the definitions and context warrant a digression. The refractive state of the eye refers to the optical distance that a person can see clearly. A change in refractive state can only occur if the relative positions or focal power of eye components change. In the art it is commonly agreed (although not necessary for this patent) that the eye lens is the only variable optical power in the eye. It changes its power by changing its shape in response to muscles surrounding it in order to allow the eye to "see" things close as well as far away. It is common to refer to the "relaxed" state as the most negative power condition that the eye can voluntarily achieve. The point in space conjugate with the retina with the eye in this state is the "far point". The process of the eye muscles making the eye more positive such that near points may be clearly seen is called "accommodation". The point in space conjugate with the retina when the eye lens is in its most positive focal power condition is called the near point. It was once thought that the refractive condition of the eye in the absence of focal cues was at the far point, or most voluntarily relaxed state. It has been shown recently that the refractive state of the eye in the absence of focal cues (e.g., insufficient illumination) will go to an intermediate "rest state of accommodation" which varies between 0 and 4 diopters negative of the far point from individual to individual. See Leibowitz and Owens, "Anomalous Myopias and the Intermediate Dark Focus of Accommodation", *Science*, Vol. 189, August 1975, pp. 646-648; Leibowitz and Owens, "Night Myopia and the Intermediate Dark Focus of Accommodation", *Journal of the Optical Society of America*, Vol. 65, No. 10, Oct. 1975, pp. 1121-1128: Hennessy, "Instrument Myopia", *Journal of the Optical Society of America*, Vol. 65, No. 10, Oct. 1975, pp. 1114-1120.

Relaxation of the eye can be accomplished by either cycloplegia or the "fogging" technique. Cycloplegia involves the use of drugs that involuntarily relax the muscles controlling the eye lens for an extended period of time, thereby attaining the most positive refractive state possible; occasionally even more positive than consciously attainable. "Fogging" involves the use of a particular sequence of apparent object distances to coax the refractive state of the eye to the far point. This latter method when implemented via a manifest (normal) eye examination yields marginally acceptable results. It is not sufficient, however, to simply present a much more distant object than the patient can see because he will regress to the rest state as described in the above references.

Although the process of accommodation is not completely understood, new simplified methods have been established to control eye accommodation. U.S. Pat. No. 3,843,240 to Cornsweet, issued Oct. 22, 1974 (and commonly assigned herewith), discloses the use of a blurred blob of light containing very little spatial "detail" as a stimulus for the relaxation of accommodation. U.S. Pat. No. 3,836,238 to Munnerlyn et al, issued Sept. 17, 1974, discloses the use of a target image which is first positioned so that the eye to be tested can focus on it, as subjectively reported by the patient, and is then moved away from the eye by an amount sufficient to blur the image (presumably as subjectively reported by the patient). The blur indicates that the patient is not focusing on the target, hopefully because he cannot relax accommodation farther.

While it has been determined that blur is a stimulus for controlling accommodation, neither of the above-mentioned inventions achieve optimal results. Conscious effort easily ignores such simple visual cues. Subjective dependence is especially undesirable with young children or others incapable of communicating.

The present invention overcomes these problems by using a totally objective technique to which almost all eyes respond rapidly and positively. A visual target image is continuously positioned close to, but offset from, the retina of the eye to be controlled. The offset puts the visual image slightly in front of the retina so that as the eye attempts to focus on the image, the accommodation of the eye will relax. The instantaneous refractive state is continuously determined by an objective refractor such as model 6600 AUTO-REFRACTOR (sold by Acuity Systems, Inc., Reston, Virginia). To maintain eye interest and to quicken response (i.e., after blinks), the image position is varied in a prescribed manner along the optical axis. This variation can take the form of a low level oscillation of the position of the image.

In addition to the use of the described oscillation to generate and hold the patient's interest, it has been found that some visual stimulii are more effective than others. The important characteristics seem to be wide spatial bandwidth and interest in the picture. Scenes of people or other objects in an unfamiliar but interesting setting seem optimal.

In the present exemplary embodiment, the refractive state control apparatus is set up to produce far point response. Even after the far point is achieved, the visual target image continues to oscillate between two optical planes, both slightly in front of the retina, so as to maintain interest and relaxation to the far point. Those skilled in the art will realize that the apparatus can be used with other objective refractors or other optical apparatus where it is necessary to control the refractive state of the eye.

The result is that the patient's response is continually coaxed toward the desired goal. If the patient accommodates, blinks, etc., the continuous refraction provides information to the refractive state control apparatus which will make the visual target image reappear near the retinal plane and again coax his response to the desired goal. This effect occurs at all points of the patient's accommodation range and therefore is continuous up to the most positive refractive state the patient can achieve. When the desired condition is achieved, the visual stimulus image then merely oscillates between two optical planes near the desired goal so as to maintain the interest and relaxation at far point.

These and other objects and advantages of the invention will become more apparent and more readily appreciated from the following detailed description of the presently preferred exemplary embodiment of the invention taken in conjunction with the accompanying drawings, of which:

Figure 1:
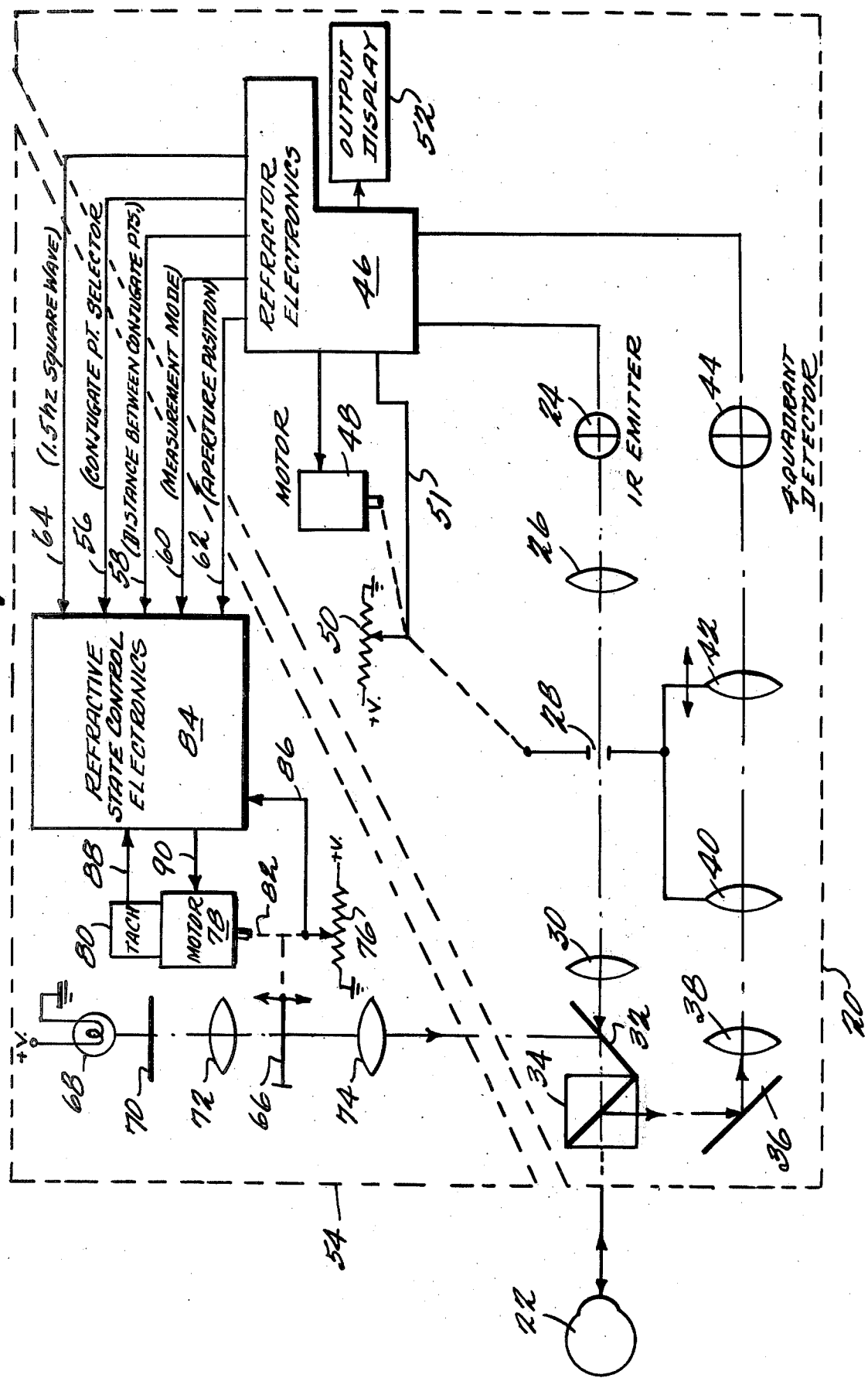
FIG. 1 is a schematic representation of the refractive state control apparatus used in conjunction with an objective refractor.

Referring first to FIG. 1, the patient places his eye 22 before the objective refractor 20. Source 24 emits infra red radiation selectively from four quadrants. Such radiation passes through lens 26, aperture 28, lens 30, and beamsplitters 32 and 34 to reach the eye 22. After passing into the eye's optical system, this radiation is reflected from the eye's retina back through the eye's optical system and on towards beamsplitter 34, which directs a part of the reflected radiation towards reflector 36. The reflected radiation then passes through lenses 38, 40 and 42 to the four quadrant photo-detector 44. The output of detector 44 is applied to the refractor electronics 46, which in turn drives motor 48. Aperture 28 and lenses 40 and 42 are driven by motor 48 in either direction parallel to the optical axis so that the position of aperture 28 is related to the instantaneous refractive power of eye 22 and therefore also related to the degree of eye accommodation. Potentiometer 50, coupled to motor 48, has a positive voltage applied to one end terminal and ground connected to the other terminal, such that the tap terminal develops a voltage related to the position of the aperture 28. This voltage, representative of the instantaneous refractive power of eye 22, is applied to the refractor electronics 46 by line 51. The refractive condition of the eye is then represented by output display 52. A number of signals from objective refractor 20 are used as inputs to the refractive state controller 54. Those skilled in the art will realize that there are potentially two meridians optically conjugate to the retina, related to the potential cylindrical characteristics of the eye lens and cornea. In the preferred embodiment, the farthest conjugate meridian is utilized. Line 56 carries a signal that represents whether the objective refractor 20 is being used to detect the nearer conjugate meridian or the farther conjugate meridian. Line 58 carries a voltage that is related to the difference in position between the nearer conjugate meridian and the farther conjugate meridian. Line 62 carries a filtered voltage similar to that on line 51 and is indicative of the position of the aperture 28. Line 60 carries a voltage indicating whether or not the objective refractor 20 is in a measuring mode. Line 64 carries a square wave produced by refractor electronics 46 (but which could be provided by a conventional oscillator) with a frequency of 1.5 Hz.

When objective refractor 20 is not in the measurement mode, target 66 of the refractive state controller 54 rests at a preselected location (optical infinity). Target 66 is illuminated by the light from lamp 68 which passes through a hot mirror and diffuser 70 and lens 72 before shining through target 66 which could be an ordinary transparency slide. The light then passes through lens 74, reflects from beamsplitter 32, passes through beamsplitter 34 and enters the eye 22. Target 66 is capable of moving between lenses 72 and 74 along the optical axis as shown by arrows. The target 66 is driven by lead screw 82 connected to the shaft of motor 78. The screw 82, in turn, is attached to the wiper of potentiometer 76 so that when the motor 78 turns, both the screw 82 and the wiper of the potentiometer 76 turn, changing the resistance of the variable terminal on potentiometer 76 with respect to the fixed resistance terminals. The fixed resistance terminals of potentiometer 76 are connected respectively to a positive voltage and ground so that the variable resistance terminal develops a voltage that is related to the position of target 66. This voltage level indicative of the position of target 66 is applied to the refractive state control electronics 84 through line 86. The speed of motor 78 is sensed by tachometer 80 whose output is also applied to the refractive state electronics 84 through line 88.

Figure 2:
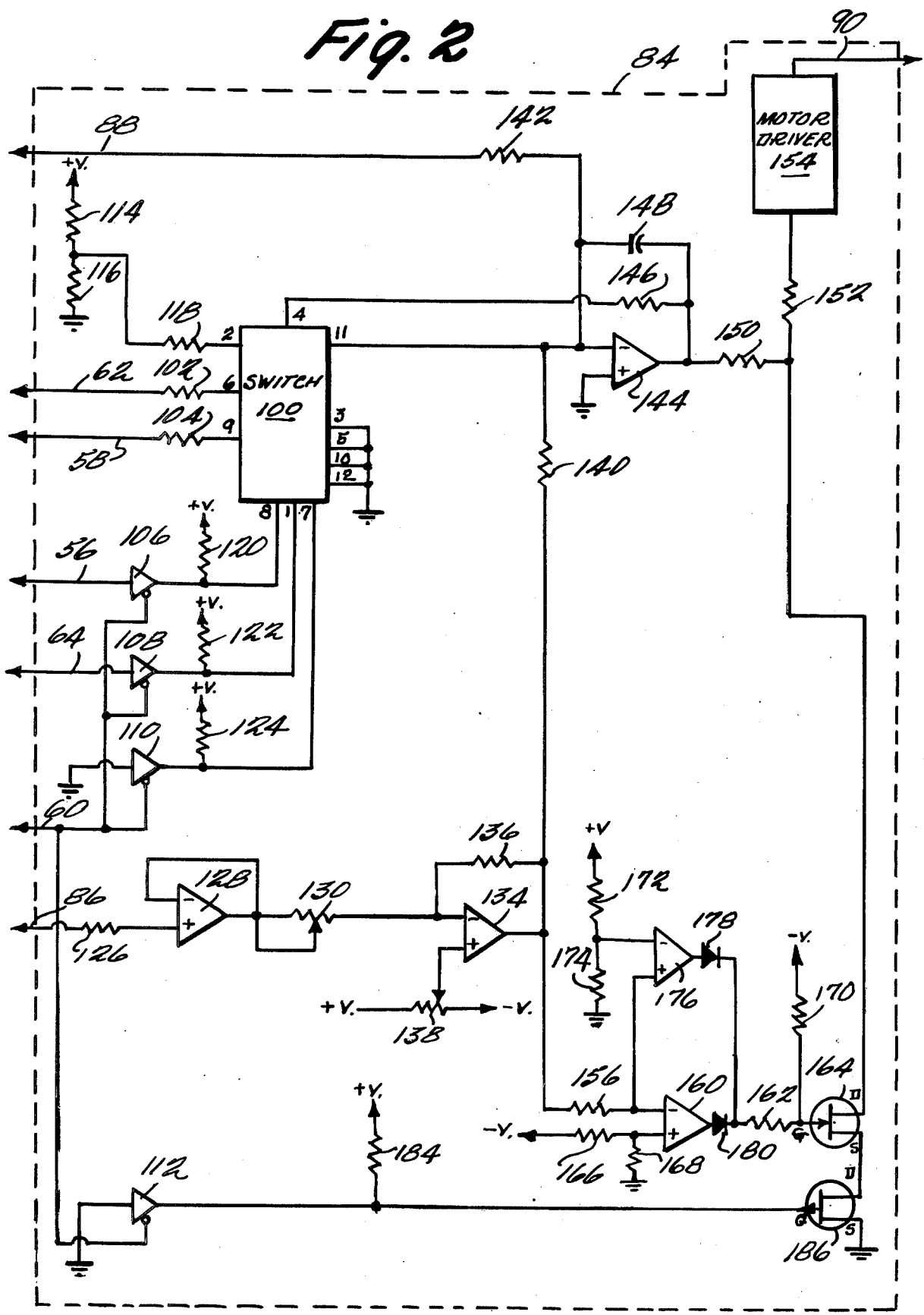
FIG. 2 is a circuit diagram of the refractive state control electronics shown in FIG. 1.

Referring now to FIG. 2, which is a circuit diagram of the refractive state control electronics 84, a filtered voltage representative of the position of aperture 28 and also one of the possible instantaneous measured conjugate points is carried on line 62 through resistor 102 to switching element 100. Switch 100 is an integrated circuit chip similar to IH5010 manufactured by Intersil. A voltage representative of the difference between the nearer conjugate meridian and the farther conjugate meridian is carried on line 58 through resistor 104 to pin 9 of switching element 100. A measurement mode signal from refractor electronics 46 is carried on line 60 to enable buffers 106, 108, 110, and 112. The measurement mode signal on line 60 is also applied through buffer 110 to pin 14 of switching element 100 thus enabling the switching element. A signal representing whether the refractor electronics 46 is indicating a nearer conjugate point or a farther conjugate point is applied on line 56 through buffer 106 to pin 8 of switching element 100. If the refractor electronics 46 indicates the nearer conjugate point, switching element 100 adds the voltage at pin 6 to the voltage at pin 9 to produce a voltage at pin 11 indicative of the farther conjugate point. If the voltage on line 56 indicates the farther conjugate point, the voltage at pin 6 of switching element 100 directly represents the position of the farther conjugate point and is not added to the voltage at pin 9 but passed directly to pin 11.

The 1.5 Hz square wave on line 64 is applied through buffer 108 to pin 1 of switching element 100. When the square wave voltage is low, the voltage at pin 2 of switching element 100 is added to the voltage at pin 11 representing the farther conjugate point. When the square wave voltage is high, the voltage at pin 2 is not added to pin 11. A constant amplitude voltage, determined by the voltage divider comprised of resistors 114 and 116, is applied to pin 2 through resistor 118.

The position of target 66 as indicated by a voltage on line 86 is applied through resistor 126 to amplifier 128. The gain of amplifier 128 is one. The output of amplifier 128 is directed through potentiometer 130 to offset amplifier 134, whose gain is controlled by the ratio of resistor 136 to potentiometer 130. The position of the visual target 66 is axially offset from the visual plane corresponding to the point conjugate to the retina by approximately ½ diopter in order to induce change in the accommodation state. The offset in the position of the visual target 66 is controlled by potentiometer 138 through which a positive or negative offset can be applied to the non-inverting input of amplifier 134. A voltage indicating the position of the visual target 66 together with the offset is thus applied through resistor 140 and summed with both the output of switch 100 on pin 11 and the tachometer output on line 88 through resistor 142. This summed voltage is applied to amplifier 144 whose gain is controlled by resistor 146.

The output of amplifier 144 is directed through resistor 146 to pin 4 of switching element 100. This voltage is summed inside switch 100 with the voltage on pin 2, modulated by the square wave on pin 1, and the voltage representing the position of the farther conjugate point. The summed total appears at pin 11. The tachometer signal on line 88 is used to improve the time response on the system. Capacitor 148 reduces system bandwidth.

The output of summing amplifier 144 is directed through resistors 150 and 152 to motor driver 154, which produces a voltage on line 90 to control motor 78 and vary the position of the visual target 66. The motor driver 154 can be a conventional servo amplifier as known in the art.

In operation, during the non-measurement mode, line 60 disables buffers 106, 108, 110, therefore turning off switch 100. The visual target 66 is positioned at a preselected location by allowing the voltage applied thru resistor 140 to drive motor 78 until the voltage at resistor 140 becomes equal to the voltage at the non-inverting input of amplifier 144.

When the measurement mode is entered, an instantaneous refraction is performed by objective refractor 20. The position of aperture 28, indicating the refractive state, is represented by a voltage level produced by potentiometer 50 connected to motor shaft 48, and this voltage level, after being passed through a two pole low pass filter located in refractor electronics 46, is applied by line 62 to switching element 100. If the refractor electronics indicates that the nearer conjugate point is being sensed, as indicated on line 56, a voltage representing the difference in position between the nearer conjugate meridian and the farther conjugate meridian (on pin 9) is added to the voltage representing the position of the aperture found on pin 6 of switch 100. This voltage plus an oscillating signal (whose frequency is controlled by pin 1 of switch 100 and whose amplitude is controlled by pin 2 of switch 100) plus the feedback from pin 4 is applied to the output pin 11.

The pin 11 output voltage is then added to the voltage at resistor 140 indicating the position of visual target 66 with the desired offset determined by potentiometer 138. These voltages together with the tachometer output are summed and amplified by amplifier 144. The output of amplifier 144 controls motor driver 154 which produces a signal on line 90 controlling motor 78. Thus, the image of visual target 66 maintains a position offset from the instantaneous refraction, the offset being in the positive direction so as to coax the eye 22 to its relaxed accommodation state. At the same time, the image of target 66 oscillates between two positions separated by approximately one-half diopter with a frequency of approximately 1.5 Hz, as controlled by the signals to pins 2 and 1 on switch 100.

The output of amplifier 134 representing the offset position of visual target 66 is also applied through resistor 156 to the inverting input of analog comparator 160 and to the non-inverting input of analog comparator 176. The output of comparator 160 is applied through diode 180 and resistor 162 to the gate of N-channel field-effect transistor 164, while the output of comparator 176 is applied to the gate of transistor 164 through diode 178 and resistor 162. Resistor 170 holds the gate of transistor 164 at a minus voltage so that transistor 164 is turned off when both of the outputs of comparator 160 and comparator 176 are negative.

In the measurement mode, buffer 112 is enabled, so that the gate of P-channel field-effect transistor 186 is placed at ground potential turning transistor 186 on, thus placing the source of transistor 164 at zero volts. A negative voltage at the non-inverting input of comparator 160 is determined by the voltage divider made up of resistors 166 and 168. When the position of visual target 66 exceeds a certain positive diopter boundary, the voltage at the inverting input of comparator 160 is more negative than the voltage at the non-inverting input of comparator 160 causing the output of comparator 160 to go positive. A positive voltage at the inverting input of comparator 176 is determined by the voltage divider made up of resistors 172 and 174. When the position of visual target 66 exceeds a certain negative diopter boundary, the voltage at the non-inverting input of comparator 176 is more positive than the voltage at the inverting input of comparator 176 causing the output of comparator 176 to go positive. A positive voltage at either the output of comparator 160 or the output of comparator 176, will cause the voltage at the gate of transistor 164 to be zero, thereby turning transistor 164 on, thus reducing the voltage between resistors 150 and 152 to approximately zero. This prevents summing amplifier 144 from commanding motor driver 154 to drive motor 78 in either direction.

When objective refractor 20 returns to the non-measurement mode, buffer 112 is deactivated permitting the gate of transistor 186 to be pulled to a positive voltage through resistor 184 which turns transistor 186 off, disconnecting the source of transistor 164 from ground which turns transistor 164 off and permits motor driver 154 to control the motion of motor 78 and thus returns visual target 66 to its preselected location.

Once the eye 22 has been drawn out to its far point refractive state, the offset image of visual target 66 merely oscillates as described above. The preferred embodiment demonstrates a simple square wave oscillation between two points. However, many other types of motion would be suitable to hold the attention of the patient.

It is also possible to include circuitry to control the intensity of the illumination from lamp 68. In the non-measuring mode, a lower level of illumination may be desirable so that the operator of the objective refractor can position the apparatus with respect to the eye 22 of the patient. A higher level of illumination for the visual target 66 may be desired in the measurement mode. Another possibility is a very reduced illumination allowing the eye to return to its "rest state".

Although only one embodiment of this invention has been described in detail above, those skilled in the art will readily appreciate that many modifications are possible without materially departing from the novel teachings and advantages of this invention. For example, much of this analog circuit could be replaced by its digital equivalent. Accordingly, all such modifications are intended to be included within the scope of this invention as defined by the following claims.

What is claimed is:

1. Apparatus for controlling the refractive state of an eye, said apparatus comprising:

a visual target;
an optical system for presenting an image of said target to said eye;
refraction means for objectively and substantially instantaneously determining said eye's refractive condition;
means coupled to said refraction means and to at least one of said target and said optical system for moving said image to a plane axially offset from the retina of said eye, said offset being in such a direction that when said eye attempts to focus on said image, the refractive state of said eye will change toward the desired goal; and
means for varying the position of said image to attract and maintain the interest of said eye.

2. Apparatus as in claim 1 wherein said means for moving said image continuously moves said image in response to the changing measured refracted state of said eye.

3. Apparatus for controlling the refractive state of an eye, said apparatus comprising:
a visual target;
an optical system for presenting an image of said target to said eye;
refraction means for objectively and substantially instantaneously determining said eye's refractive condition; and
means coupled to said refraction means and to at least one of said target and said optical system for moving said image to a plane axially offset from the retina of said eye, said offset being in such a direction that when said eye attempts to focus on said image, the refractive state of said eye will become more negative and, therefore, approach the far point; and
means for varying the position of said image to attract and maintain the interest of said eye.

4. Apparatus as in claim 3 wherein said refraction means comprises an objective refracting device for determining the conjugate point farthest from said eye when said eye has two conjugate points as in an astigmatic eye.

5. Apparatus as in claim 3 wherein said means for moving said image continuously moves said image in response to the changing measured refracted state of said eye.

6. Apparatus as in claim 3 wherein said means for moving and said means for varying comprise:
a motor for moving said target within said optical system;
position sensing means having an output related to the position of said target;
offset means for controlling the degree to which the plane of said image is axially separated from the plane of said retina; and
summation means connected to control said motor in response to the sum of signals from at least said refraction means, said position sensing means, said offset means, and said means for varying.

7. Apparatus as in claim 3 wherein said image oscillates at a frequency between ½ to ten Hertz.

8. Apparatus as in claim 3 wherein said image oscillates between two positions, one-quarter to one diopter apart.

9. Apparatus as in claim 3 wherein said image is axially offset from said retina by zero to one diopter.

10. Apparatus for controlling the refractive state of an eye, said apparatus comprising:
a visual target;
an optical system for presenting an image of said target to said eye;
refraction means for objectively and substantially instantaneously determining said eye's refractive condition;
means for positioning said image in a visual plane axially offset from the retina of said eye, said offset being in such a direction that when said eye attempts to focus on said image the refractive state of said eye will become more negative and, therefore, approach the far point; and
means for varying the position of said image to attract and maintain the interest of said eye.

11. Apparatus as in claim 10 wherein said refraction means comprises an objective refractor for determining the conjugate point farthest from said eye.

12. Apparatus as in claim 10 wherein said positioning means and said means for varying comprise:
a motor connected to said target for controlling the position of the latter within said optical system;
means for sensing the position of said target;
offset means for controlling the degree to which the plane of said image is axially offset from the retina of the eye; and
summation means connected to control said motor in response to the sum of signals from at least said refraction means, said means for sensing, said offset means, and said means for varying.

13. Apparatus as in claim 10 wherein said means for positioning continuously positions said target image in relation to the changing conjugate point of said eye.

14. Method for controlling the refractive state of an eye, said method including:
objectively and substantially instantaneously measuring said eye's refractive state with refraction means;
positioning the image of a target at a visual plane axially offset from the retina of the eye, said offset being in such a direction that when said eye attempts to focus on said image the refractive state of said eye will change toward the desired goal; and
varying the position of said image to attract and maintain the interest of said eye.

15. Method as in claim 14 wherein the determination of said eye's refractive condition is made continuously, and the positioning of said image in response to the changing said conjugate point occurring continuously.

16. Method for controlling the refractive state of an eye, said method including:
objectively and substantially instantaneously measuring said eye's refractive state with refraction means;
positioning the image of a target at a visual plane axially offset from the retina of said eye, said offset being in such a direction that when said eye attempts to focus on said image the refractive state of said eye will become more negative and, therefore, approach the far point; and
varying the position of said image to attract and maintain the interest of said eye.

17. Method as in claim 16 wherein the determination of said eye's refractive condition is made continuously, and the positioning of said image in response to the changing said conjugate point occurring continuously.

18. Method as in claim 16 wherein said determination of said eye's refractive condition is accomplished by determining the location of the conjugate point farthest from said eye.

19. Method as in claim 19 wherein said image oscillates at a frequency of one to two Hertz.

20. Method as in claim 19 wherein said image oscillates between two positions one-quarter to one-half a diopter apart.

21. Method as in claim 16 wherein said image is offset from said retina by one-eighth to one-half a diopter.

22. Method for controlling the refractive state of an eye, said method including:
    measuring said eye's refractive state with refraction means by determining the location of the conjugate point farthest from said eye;
    positioning the image of a target at a focal plane offset from the retina of said eye, said offset being in such a direction so that when said eye attempts to focus on said image, the accommodation of said eye will become more negative and, therefore, approach the far point; and
    varying the position of said image to attract and maintain the interest of said eye.

23. Method as in claim 22 wherein all steps of the method are practiced continuously throughout the desired control period.

24. In an apparatus for measuring an optical parameter of an eye where it is desired to make such measurement with said eye in a predetermined refractive state, the improvement including an apparatus for automatically controlling the accommodation of said eye comprising:
    a visual target;
    an optical system for presenting the image of said target to said eye;
    refraction means for objectively and substantially instantaneously determining said eye's refractive condition;
    means for moving the image of said target to a plane axially offset from the retina of said eye, said offset being in such a direction that when said eye attempts to focus on said image, the refractive state of said eye will change toward the desired goal; and
    means for varying the position of said image to attract and maintain the interest of said eye.

25. In an apparatus for measuring an optical parameter of an eye where it is desired to make such measurement with said eye at its far point, the improvement including an apparatus for automatically controlling the refractive state of said eye comprising:
    a visual target;
    an optical system for presenting the image of said target to said eye;
    refraction means for objectively and substantially instantaneously determining said eye's refractive condition;
    means for moving the image of said target to a plane axially offset from the retina of said eye, said offset being in such a direction that when said eye attempts to focus on said image, the refractive state of said eye will become more negative and, therefore, approach the far point; and
    means for varying the position of said image to attract and maintain the interest of said eye.

26. In an apparatus for measuring an optical parameter of an eye where it is desired to make such measurement with said eye at its far point, the improvement including an apparatus for automatically controlling the refractive state of said eye comprising:
    a visual target;
    an optical system for presenting the image of said target to said eye;
    refraction means for objectively and substantially instantaneously determining the said eye's refractive condition;
    means for moving the image of said target to a plane axially offset from the retina of said eye, said offset being in such a direction so that when said eye attempts to focus on said image, the refractive state of said eye will become more negative and, therefore, approach the far point; and
    means for oscillating the position of said image to attract and maintain the interest of said eye.

* * * * *